US009258720B2

(12) United States Patent
Kokovidis et al.

(10) Patent No.: US 9,258,720 B2
(45) Date of Patent: Feb. 9, 2016

(54) THROUGHPUT-BASED ACTIVE MODE TRIGGER

(75) Inventors: Georgios Kokovidis, Waltham, MA (US); Kurt Robert Bianculli, Marblehead, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 173 days.

(21) Appl. No.: 14/234,432

(22) PCT Filed: Aug. 3, 2011

(86) PCT No.: PCT/US2011/046406
§ 371 (c)(1),
(2), (4) Date: Jan. 23, 2014

(87) PCT Pub. No.: WO2013/019225
PCT Pub. Date: Feb. 7, 2013

(65) Prior Publication Data
US 2014/0153434 A1    Jun. 5, 2014

(51) Int. Cl.
*G08C 17/00*      (2006.01)
*H04W 24/02*     (2009.01)
(Continued)

(52) U.S. Cl.
CPC ............ *H04W 24/02* (2013.01); *A61B 5/0015* (2013.01); *H04L 67/12* (2013.01);
(Continued)

(58) Field of Classification Search
USPC .......................... 370/229, 241, 252, 311, 328
See application file for complete search history.

(56) References Cited

U.S. PATENT DOCUMENTS

| | | | |
|---|---|---|---|
| 5,355,366 A * | 10/1994 | Li | H04L 12/6402 370/528 |
| 6,192,230 B1 | 2/2001 | van Bokhorst et al. | |
| 8,170,624 B1 * | 5/2012 | Huang | H04W 52/0209 455/127.1 |
| 2003/0114204 A1 | 6/2003 | Allen et al. | |

(Continued)

FOREIGN PATENT DOCUMENTS

WO    WO2007/121763    11/2007
WO    WO2009/141504    11/2009

OTHER PUBLICATIONS

Moshaddique Al Ameen et al. "A Power Efficient Mac Protocol for Implant Device Communication in Wireless Body Area Networks". Consumer Communications and Networking Conference (CCNC), 2011 IEEE, IEEE, Jan. 9, 2011, pp. 1155-1160, XP031865871, DOI: 10.1109/CCNC.2011.5766358 ISBN: 978-1-4244-8789-9 Section IV.

*Primary Examiner* — Kwang B Yao
*Assistant Examiner* — Nguyen Ngo
(74) *Attorney, Agent, or Firm* — Jones Day

(57) ABSTRACT

A method and apparatus for reducing gaps in data transmission between a device and at least one wireless access point connecting the first device to a central monitoring system. The device includes a radio that enables bidirectional data communication between the device and the at least one wireless access point, the radio being able to operate in a power save mode and an active transmission mode. A control processor selectively monitors a type and amount of data being transmitted between the radio and the at least one wireless access point to predict an occurrence of a gap in data transmission between the device and the at least one access point. The control processor, in response to predicting a gap in data transmission, automatically switches an operational mode of the radio from the power save mode to the active transmission mode for a predetermined amount of time enabling full bidirectional communication between the device and the at least one wireless access point for the predetermined amount of time preventing the gap in data transmission.

22 Claims, 6 Drawing Sheets

(51) Int. Cl.
*H04W 52/02* (2009.01)
*H04L 29/08* (2006.01)
*G06F 19/00* (2011.01)
*A61B 5/00* (2006.01)
*A61B 5/0215* (2006.01)
*A61B 5/1455* (2006.01)

(52) U.S. Cl.
CPC ..... *H04W 52/0235* (2013.01); *H04W 52/0238* (2013.01); *A61B 5/0006* (2013.01); *A61B 5/0215* (2013.01); *A61B 5/14551* (2013.01); *A61B 2560/0209* (2013.01); *G06F 19/3418* (2013.01); *Y02B 60/50* (2013.01)

(56) References Cited

U.S. PATENT DOCUMENTS

| | | | | |
|---|---|---|---|---|
| 2010/0297932 A1* | 11/2010 | Golshenas | ........ | H04W 52/0229 455/3.01 |
| 2011/0185202 A1* | 7/2011 | Black | ................ | H04W 52/0258 713/320 |
| 2011/0292854 A1* | 12/2011 | Terry | ..................... | H04L 5/001 370/311 |
| 2013/0028126 A1* | 1/2013 | Kazmi | ............. | H04W 36/0088 370/252 |
| 2013/0170418 A1* | 7/2013 | Stauffer | ............ | H04W 52/0229 370/311 |

* cited by examiner

THROUGHPUT-BASED ACTIVE MODE TRIGGER

The present application is a 35 USC §371 national stage application of International Application No. PCT/US2011/046406, filed Aug. 3, 2011, the entirety of which is incorporated herein by reference.

FIELD OF THE INVENTION

This invention concerns a system and method for minimizing gaps in data transmission between devices in a wireless communication environment

BACKGROUND OF THE INVENTION

Monitoring patients presents challenges to healthcare professionals that are charged with patient care. These challenges are accentuated when the patients being monitored are ambulatory because the devices used for monitoring patient parameters are also required to be movable so that the patient is not confined to a particular bed in a particular care unit. There are a plurality of portable patient monitoring devices able to monitor different patient parameters. The monitored patient parameters may be transmitted over a wireless communications network for receipt by a central monitoring station. In order for these monitors to remain portable and enable patients to be ambulatory, these monitoring devices often include rechargeable batteries. However, a drawback associated with portable patient monitors that wirelessly transmit data is the need to maintain the monitors in a lower power state to maximize battery life while ensuring that there are no gaps in the data being transmitted and/or received by the monitors.

Furthermore, in order for patients to remain ambulatory, they should be able to wireless transmit data from and receive data at their respective monitoring devices. In a healthcare environment that is outfitted with a wireless network (e.g. 802.11a/b/d/g/i/n, etc), in order to consistently monitor the patients when they are moving between different care units, there are a plurality of access points positioned at various areas throughout the healthcare environment. The plurality of access points are coupled to at least one communications network that includes at least one monitoring station for collecting patient data. The collected patient data may, for example, be displayed on a display device or stored in a patient information database for the purpose of creating a patient healthcare record. In order for this patient data to be reliably collected, the portable patient monitors can selectively communicate with a respective one of the access points to transmit and receive data therebetween. While the patient is moving around the healthcare enterprise, the communication may be selectively handed off between successive access points depending on the proximity of the portable patient monitor to the respective access point. Proximity is determined based on a received signal strength indicator (RSSI) which is a measure of power. Thus, the portable patient monitors look for the highest RSSI value (or in some cases, the least negative RSSI value) which determines and identifies the "closest" access point. While RSSI value successfully determines the access point to which the portable patient monitor will connect in order to prevent a gap in data transmission, it is unable to avoid the transmission gap that often occurs when the portable patient monitor has already identified that a particular access point is the "closest" access point. Thus, a need exists to improve data transmission between monitoring devices and access points, when proximity to an access point is not the cause of the transmission gap. A system according to invention principles addresses deficiencies of known systems to reduce transmission gaps between portable monitoring devices that are connected to a central monitoring station via at least one wireless access point.

SUMMARY OF THE INVENTION

In one embodiment, an apparatus for reducing gaps in data transmission between a device and at least one wireless access point is provided. The device includes a radio that enables bidirectional data communication between the device and the at least one wireless access point, the radio being able to operate in a power save mode and an active transmission mode. A control processor selectively monitors a type and amount of data being transmitted between the radio and the at least one wireless access point to predict an occurrence of a gap in data transmission between the device and the at least one access point. The control processor, in response to predicting a gap in data transmission, automatically switches an operational mode of the radio from the power save mode to the active transmission mode for a predetermined amount of time enabling full bidirectional communication between the device and the at least one wireless access point for the predetermined amount of time preventing the gap in data transmission.

In another embodiment, a method of reducing gaps in data transmission between a device and at least one wireless access point connecting the first device to a central monitoring system. The method comprises the activities of monitoring, by a control processor, a type and amount of data being transmitted between a radio of the device and the at least one wireless access point. The method further includes predicting an occurrence of a gap in data transmission between the device and the at least one access point and automatically switching an operational mode of the radio from power save mode to active transmission mode for a predetermined amount of time in response to predicting a gap in data transmission. Full bidirectional communication is enabled between the device and the at least one wireless access point for the predetermined amount of time preventing the gap in data transmission.

In another embodiment, an apparatus for reducing gaps in data transmission between a device and at least one wireless access point is provided. The device includes a radio that enables bidirectional data communication between the device and the at least one wireless access point. The radio is able to operate in a power save mode and an active transmission mode. A control processor selectively monitors data being transmitted between the radio and the at least one wireless access point to detect an occurrence of a gap in data transmission between the device and the at least one access point. The control processor, in response to detecting a gap in data transmission, automatically switches an operational mode of the radio from the power save mode to the active transmission mode for a predetermined amount of time enabling communication between the device and the at least one wireless access point for the predetermined amount of time.

DETAILED DESCRIPTION

Patients that are admitted to a healthcare facility such as a hospital are continuously monitored. This continual monitoring is a data intensive task that should occur no matter where the patient is located within the facility. To achieve this goal, healthcare facilities have been outfitted with a network of wireless access points that enable wireless communication between a central monitoring station and a plurality of portable patient monitoring devices. The portable patient monitoring devices may be powered by a rechargeable battery source and thus have a finite amount of power with which to operate to accomplish their monitoring functions as well as communication functions. Thus, it is desirable to minimize the power consumption of the communication circuitry of these portable patient monitoring devices because continual operation thereof places a significant drain on the power source of the portable patient monitoring device. To this end, the radio circuitry of the portable patient monitoring devices are conventionally set to operate in a power-save mode. However, in power save mode, a gap in data transmission from or receipt by the portable patient monitoring devices may occur because the portable patient monitoring devices rely on a signal from a respective access point to enable transmission/receipt of data. If this signal is not received or otherwise not detected by the portable patient monitoring device, the device will remain in power save mode and will not transmit or receive data thereby resulting in a gap in patient monitoring data intended to be transferred between the portable patient monitor and the central monitoring station. The present system advantageously and automatically resolves this problem by monitoring throughput of data and use of the detected data throughput level to control when the portable patient monitor should move between the power save (default) operating mode and an active mode during which the communication circuitry is fully operational and data is continuously transmitted and/or received by the portable patient monitoring device. The system further advantageously causes the portable patient monitoring device to remain in active mode for a predetermined amount of time thereby ensuring that the intended data transmission occurs prior to automatically switching back to the default power save mode of operation. Thus, the limited transition into active mode advantageously ensures that the intended data transmission will occur without sacrificing the battery life of the portable patient monitoring device.

Figure 1:
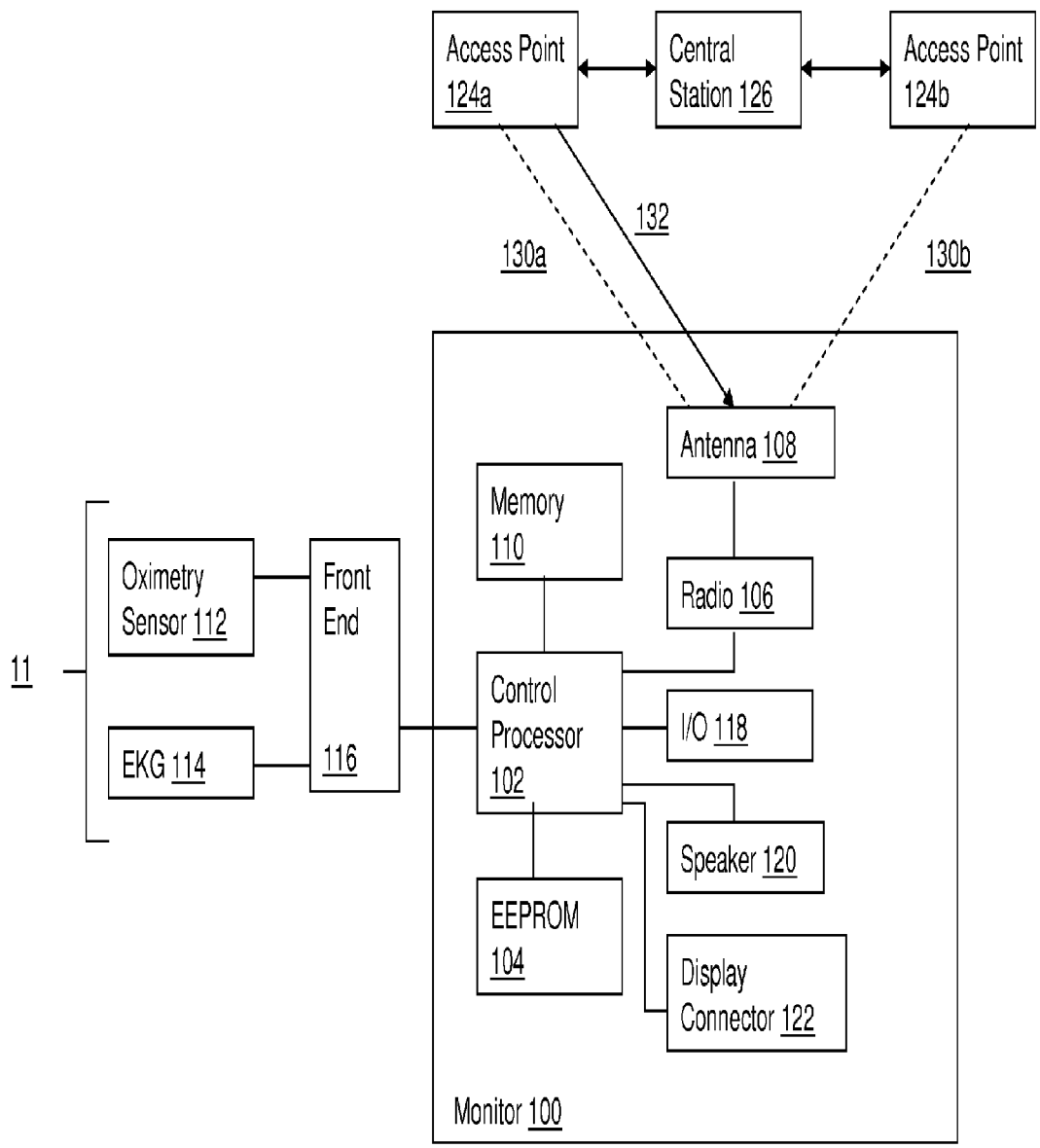
FIG. 1 is a block diagram of a portable patient monitoring device according to invention principles.

FIG. 1 is an exemplary embodiment of a portable patient monitor (hereinafter, "monitor") 100 according to invention principles. The monitor 100 includes a control processor 102 and an electrically erasable programmable read only memory (EEPROM) 104 that includes configuration data used by the control processor 102 for controlling monitor operation. The monitor 100 includes a front end 116 that interfaces between a plurality of patient parameter sensors 111 and the monitor 100. As shown herein patient parameter sensors 111 may include, but are not limited to an oximetry sensor 112 that senses an amount of oxygen in a patients blood and an electrocardiogram (EKG) 114 that selectively monitors electrical impulses generated by the patients heart. The inclusion of these types of patient sensors 111 is for purposes of example only and any type of patient sensor may be coupled to the front end 116 of the monitor 100 in addition or in place of the oximetry sensor 116 and EKG 114. Additional patient sensors 111 may include at least one of (a) Respiration sensor; (b) Non Invasive Blood Pressure (NIBP) sensor; (c) Invasive Blood Pressure (IBP) sensor; (d) End Tidal Carbon Dioxide (eTCO2) sensor and (e) temperature sensor.

The front end 116 is electrically coupled to the control processor 102. The control processor 102 may provide control information for controlling the operation of the respective patient sensors 111 coupled to the front end 116. The front end 116 also receives data sensed by the patient sensors 111 which is provided back to the patient monitor 100 as patient parameter data. The control processor 102 causes the received patient parameter data to be stored in a memory 110 coupled to the control processor 102. The monitor 100 may also include at least one input/output (I/O) port 118 coupled to the control processor 102 allowing a user to selectively interact with the monitor 100 via an I/O device connected thereto. I/O devices may include, but are not limited to at least one of (a) a keyboard; (b) a mouse; and (c) a touchpad. For example, a user may selective modify operating instructions associated with the patient sensors 111 coupled to the monitor 110. Additionally, a speaker 120 may be coupled to the control processor 102 for outputting an audible alert to notify a user that a certain event is occurring. For example, data sensed by the EKG 114 may be determined to be indicative of atrial fibrillation requiring immediate attention. In this example, the control processor 102 may cause the speaker to output a particular type of alarm to let a user know this condition is occurring in the patient being monitored. Additionally, the patient monitor 100 may include a display connector 122 enabling a display device to be coupled to the monitor 100 allowing for display of at least one of (a) patient parameter data being monitored and (b) device-specific operating information. Alternatively, the monitor 100 may include a display integrally formed therewith.

The monitor 100 includes a radio 106 and an antenna 108 coupled thereto. The radio 106 selectively enables bidirectional communication between the monitor 100 and a central monitoring station 126 via a plurality of wireless access points 124a, 124b. While only two wireless access points 124a and 124b are shown, one skilled in the art of wireless network design would appreciate that any number of wireless access points may be included depending on the size of the environment in which communication is to occur. The wireless data transmission employed by the radio 106 may be in accordance with the Wireless LAN Medium Access Control and Physical Layer Specification known as IEEE Standard 802.11. This may include, but not limited to, communication protocols such as (a) 802.11a, (b) 802.11b, (c) 802.11g and (d) 802.11n. The 802.11 protocol enables the radio 106 to associate the monitor 100 with a respective one of the plurality of access points 124a in a known manner. If the RSSI value of the first wireless access point falls below a threshold RSSI value (typically −75 dBm), the radio 106 automatically initiates a scan for additional access points with higher (less negative) RSSI values to maintain communication with the central station 126. In the event that the RSSI signal falls below the threshold, the radio 106 will transmit a disassociate signal to the first access point 124a and an associate (or reassociate) signal to a second wireless access point 124b determined to be closer to the monitor and have a higher RSSI. Upon authentication by the second wireless access point 124*b*, the monitor 100 will be able to bidirectionally communicate with the central station 126 via the second access point 124*b*.

In a healthcare environment, it is essential to consistently monitor patient parameters and insure that healthcare professionals have access to this data in real-time so as to quickly and effectively provide treatment to a patient should the need arise. Unfortunately, bidirectional radio transmission is a power-intensive process and, if the radio 106 is configured to actively transmit and/or receive data at all times, the power source of the monitor 100 will be drained at a quicker rate than is acceptable. Thus, the radio 106 is configured according to the 802.11 protocol to operate in a power-save mode (PSM). In PSM, the radio 106 is in a "sleep mode" at all times except when needed to transmit and/or receive data from a wireless access point. In sleep mode, the radio may selectively receive beacon packets 130 from an access point to which the monitor 100 is associated. For purposes of example, the monitor 100 will be discussed as being associated with the first access point 124*a*. However, the principles described herein may be applied when associated with any access point connected to the central station 126. Beacon packets 130 may include any information indicating that there are data buffered at the access point 124*a* waiting for transmission to the monitor 100 or that data are being requested from the monitor 100. When the radio 106 receives a beacon packet 130 from an access point 124*a*, the radio 106 automatically transmits a PS_Poll message 132 to the access point 124*a*. Transmission of the PS_Poll message 130 results in the radio 106 emerging from "sleep mode" into "active mode" to enable bidirectional communication between the radio 106 and the wireless access point 124*a*. The PS Poll message 132 instructs the wireless access point 124*a* to transmit the buffered data stored at the access point 124*a* or transmit the request for data from the access point 124*a* to the radio 106. This process continues until all the data buffered at the access point 124*a* has been transmitted to and received by the radio 106 of the monitor 100.

The radio 106 also measures a level of data throughput in a receive mode (RX mode) which includes data throughput received by the radio 106 transmitted from the wireless access point 124*a* while the radio 106 is in PSM. Data throughput may be measured in bits transmitted per second (b/s) and include transmission control protocol (TCP) data governing the connection between the monitor 100 and the access point 124*a* and/or the central station 126. Additionally, throughput data being measured may include at least one of (a) User Datagram Protocol (UDP) data; (b) Address Resolution Protocol (ARP) data; (c) Internet Group Management Protocol (IGMP) data; and (d) Internet Control Message Protocol (ICMP) data. The throughput data level may be indicative of connection strength between the monitor 100 and the access point 124*a*. A predetermined range of throughput data values is stored for use in determining the connection strength of the radio 106 to the access point 124*a*. If the measured throughput data value is within the predetermined range, it is indicative that there will not be any gaps in data transmitted from the access point 124*a* to the monitor 100. In one embodiment, the predetermined range used for comparing throughput data transmitted by the access point ranges between substantially 1000 b/s and 20000 b/s. If the radio 106 determines that the throughput data value is at least one of below the lower limit of the predetermined range of throughput data or above the upper limit of the predetermined throughput range, it is indicative that a gap in transmission has occurred or may occur. If the measured throughput level is below the lower limit of the range, it may be indicative of a beacon transmission failure from the access point 124*a*. If the measured throughput level is above the upper limit of the range, it may be a predictive indicator that beacon transmission will not occur as expected.

The radio 106 may also measure a level of data throughput in a transmission mode (TX mode) which includes data throughput transmitted by the radio 106 to the wireless access point 124*a* while the radio 106 is in PSM. The throughput data being monitored in this embodiment may be any of the throughput data types described above. A predetermined range of throughput data values is stored for use in determining the connection strength of the radio 106 to the access point 124*a*. If the measured throughput data value is within the predetermined range, it is indicative that there will not be any gaps in data transmitted by the radio 106 to the access point 124*a*. In this embodiment, the predetermined range used for comparing throughput data transmitted by the radio 106 to the access point ranges between substantially 2500 b/s and 60000 b/s. If the radio 106 determines that the throughput data value is at least one of below the lower limit of the predetermined range of throughput data or above the upper limit of the predetermined throughput range, it is indicative that a gap in transmission has occurred or may occur.

The predetermined throughput data ranges described above are described for purposes of example only. The predetermined throughput data ranges for a particular monitor may be based on the average amount of data transmitted by the monitor. For example, the transmission and receipt (TX/RX) ranges described above may be associated with a monitor having an average TX/RX value of substantially 25000 bps. Thus, the predetermined range of acceptable values may include the average TX/RX rate at substantially a midpoint thereof. For example, if a monitor has an average TX/RX rate 100000 bps, the predetermined range of throughput data values may be between substantially 40000 bps and 160000 bps. In another embodiment, a monitor may monitor a plurality of different types of data in different monitoring modes and each monitoring mode may include a unique predetermined range of throughput data values based on the type and amount of average data that is transmitted and received by the radio of the monitor.

The radio 106 automatically switches from a PSM to an active mode for a predetermined amount of time (~120 seconds) when the throughput data value in either the RX mode or TX mode is below the lower limit of the predetermined range or when the throughput data value is above the upper limit of the predetermined range. The radio 106 utilizes an active mode timer which is initiated in response to the measurement of throughput data. Upon entering active mode, the radio 106 no longer needs to rely on beacon packets 130 to wake up and initiate a transmission of data. Rather, in active mode, the radio 106 automatically transmits and receives data continually. Once in active mode, any data buffered at the access point 124*a* and addressed to the monitor 100 is automatically transmitted to the monitor 100 thereby preventing a gap in data transmission that might have otherwise occurred. At the expiration of the predetermined amount of time as determined by the active mode timer, the radio 106 automatically switches from active mode to the power save mode to continue the default operation. In another embodiment, switching from active mode into power save mode may occur prior to expiration of the active mode time period if the radio 106 determines that no additional data is scheduled for transmission from the access point 124*a* thus further minimizing the drain on the power source of the monitor 100.

The automatic initiation of a finite active mode time period advantageously reduces a number of gaps in data transmission between the monitor 100 and the access point 124a while minimizing the effect on the power source of the monitor. This further enables the patient connected monitor to be freely mobile within a healthcare environment for extended periods of time while insuring that the patient is continually monitored with few or no gaps in waveform data.

Figure 2:
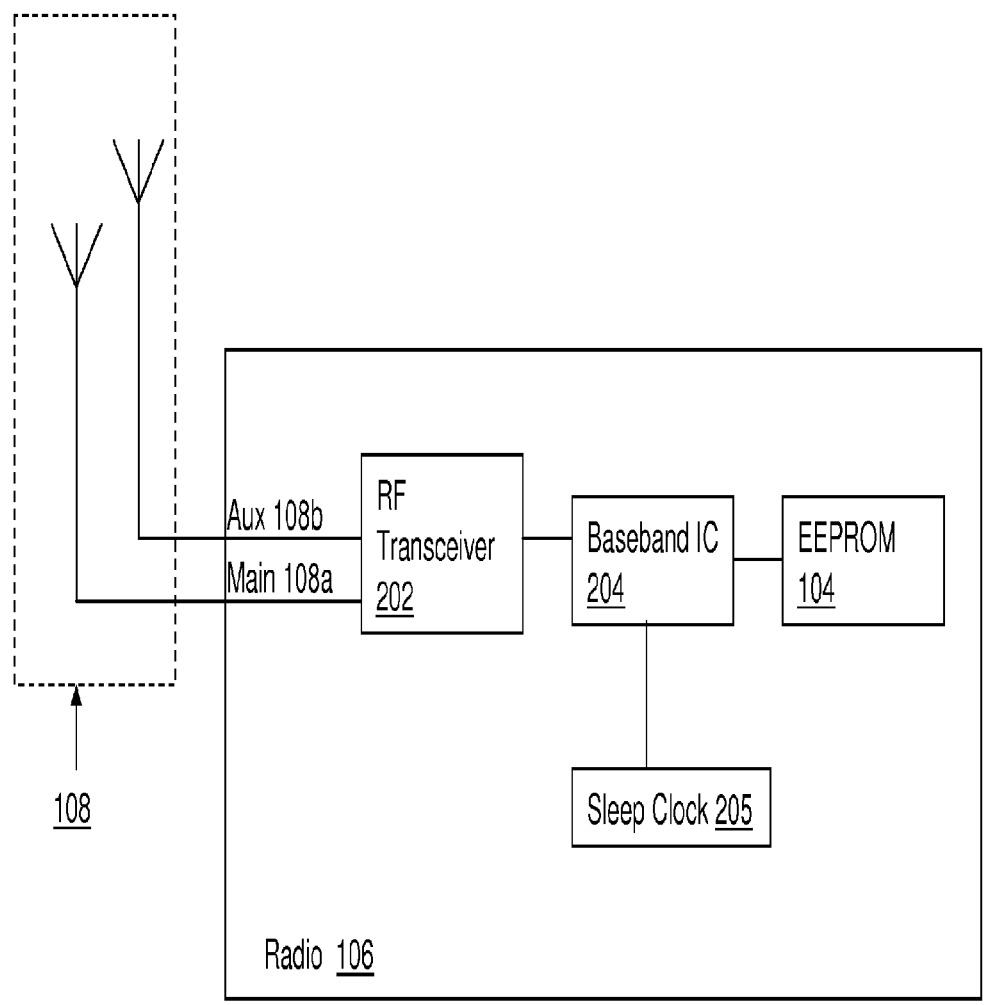
FIG. 2 is a block diagram of an exemplary radio circuit of a portable patient monitoring device according to invention principles.

FIG. 2 is an exemplary block diagram of the radio 106 described above with respect to FIG. 1. The radio 106 may be a System-in-a-Package (SiP) that provides a low-power radio integrated circuit able to bidirectionally communicate according to any IEEE 802.11 protocol (e.g. 802.11a, 802.11b, 802.11g and/or 802.11n) including any amendments made thereto (e.g. 802.11d world wide use, 802.11e QoS and 802.11i—WEP Alternative). The radio 106 may be formed as a no-host-load system architecture that enables the host to sleep while the radio 106 is in PSM and is actively monitoring beacon packets from access points. An antenna 108 is electrically coupled to the radio 106. As shown herein the antenna 108 may include a main antenna 108a and an auxiliary antenna 108b. The antennas 108a and 108b may, for example, be connected to an output of the radio 106 via micro coax cables terminating to a U.FL style connector at the feed point of the antennas. The radio 106 supports communication with the control processor 102 (FIG. 1) via a serial peripheral interface (SPI) bus. Alternatively, the radio may support communication with the control processor 102 via a secure digital input output (SDIO) card or Universal Asynchronous Receiver/Transmitter (UART). The system further includes an external crystal oscillator and 2 capacitors. The crystal oscillator provides an accurate time source which drives the operation of the sleep clock 205. The sleep clock 205 determines a time at which the radio 106 should "wake up" in order to listen for and receive a beacon from an access point.

The radio 106 includes a Radio EEPROM 206 that includes instructions stored therein for controlling the operation of the radio 106. A baseband integrated circuit (IC) 204 is coupled to the Radio EEPROM and selectively operates in a known manner to control the frequency of the signals transmitted from and received by the radio 106. A sleep clock 205 selectively controls when the baseband IC 204 will awake from power save mode to scan for beacon packets originating from an access point 124a. For example, the sleep clock 205 may automatically wake the baseband IC at one hundred millisecond (100 ms) intervals to scan for beacon packets. A radio frequency (RF) transmitter 202 is coupled to the baseband IC 204. The baseband IC 204 causes the RF transceiver 202 to at least one of transmit and/or receive data. Additionally, the baseband IC 204 may control the RF transceiver 202 to scan for data representing beacon packets from at least one wireless access point.

In operation, the radio EEPROM 206 may include a set of instructions for switching the baseband IC 204 and the RF transceiver 202 from a power save mode to an active transmission mode at a predefined interval. When in power save mode, the radio 106 should have an average power consumption below 2 mW. The average power consumption is achieved because the radio 106 only interfaces with the control processor 102 of the monitor 100 (FIG. 1) when a valid data packet is received and thereby complies with a "wake on receive" mode. The radio 106 continually processes 802.11 beacons received at the antenna 108 and which originate from the access point 124a and allows the host processor to sleep and remain in power save mode, thereby increasing battery life of the monitor 100.

The radio EEPROM 206 may include operating instructions that initiate an active mode trigger algorithm that actively monitors an amount of throughput data received by the RF transceiver 202 via the antenna 108. The radio EEPROM 206 may include a range of throughput data values that indicate proper transmission of data between the access point 124a and the monitor 100. If the baseband IC detects that the throughput data values fall below the lower limit of the acceptable range or exceed the upper limit of the acceptable range, the baseband IC 204 is automatically switched into active transmission mode for a predetermined time period thus enabling full transmission and receipt of data by the RF transceiver 202. This insures that any data scheduled to be transmitted from the access point will be received by the radio 106 for its intended purpose. Additionally, switching into active mode will insure that any data scheduled to be transmitted from the monitor to the access point will be transmitted for receipt by the access point.

There are a plurality of events that may lead to the throughput data being processed by the radio 106 at least one of falling below or exceeding the predetermined range of acceptable throughput data values. This may include communication and/or configuration errors associated with the power save protocol implemented in the wireless network environment. For example, the access point may not transmit the beacon packet at the expected time. In this instance, the throughput data received and monitored by the radio 106 may fall below the acceptable range of throughput data values. Upon switching into active mode for the predetermined amount of time, data transmission (or receipt) automatically occurs as expected in an attempt to prevent a gap in transmission by capturing the data that was expected to be transmitted at the given interval.

Another event that may result in initiation of the active mode trigger algorithm occurs when the monitor disassociates from an access point just after sending a PS_Poll message but prior to transmission of the buffered data. The access point will temporarily increase an amount of throughput data prior to the expected data transmission resulting in the throughput data monitored by the radio exceeding the upper limit of the acceptable throughput data range. Upon dissociation, the buffered data scheduled for the monitor is purged thus causing a gap in data transmission. However, upon detecting the temporary increase in throughput data and switching into active transmission mode for the predetermined amount of time, the monitor will receive the data buffered at the access point prior to dissociating from the access point.

A further event that may result in the initiation of the active mode trigger algorithm occurs when the access point has communicated a "Request to Send" (RTS) message indicating that data is buffered for transmission to the monitor. In proper operation, the radio 106 of the monitor 100 would transmit a "Clear to Send" (CTS) message indicating that the monitor is ready to receive the data. In the event that monitor 100 fails to send the CTS message, the throughput data being transmitted by the monitor may fall below the acceptable range. Should a plurality of RTS messages be received without any CTS message returned, the active mode transmission algorithm may be initiated to enable full duplex communication between the monitor and the access point.

Another event that may result in the initiation of the active mode trigger algorithm occurs when the radio 106 has communicated a "Request to Send" (RTS) message indicating that data is buffered in the monitor for transmission to an access point. In proper operation, the access point would transmit a "Clear to Send" (CTS) message indicating that the access point is ready to receive the data. In the event that radio 106 fails to receive the CTS message, the throughput data being transmitted by the access point may fall below the acceptable range. Should a plurality of RTS messages be transmitted by the radio without any CTS message returned by the access point or received by the monitor 100, the active mode transmission algorithm may be initiated to enable full duplex communication between the monitor and the access point.

FIGS. 3-6 are flow diagrams describing the algorithms implemented by the monitor 100 of FIG. 1 to minimize gaps in data transmission between the monitor 100 and a plurality of access points 124a and 124b. The algorithms described in FIGS. 3-6 will be discussed with respect to the circuits and components described above with respect to FIGS. 1 and 2.

Figure 3:
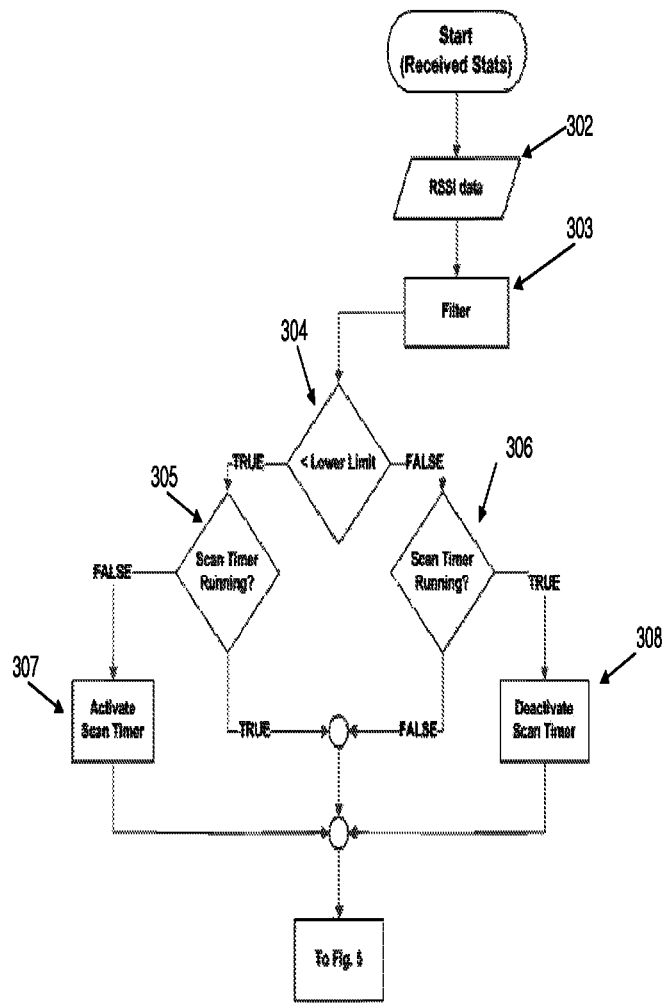
FIG. 3 is a flow diagram detailing an operation of a portable patient monitoring device according to invention principles.

FIG. 3 is an exemplary roaming algorithm that may be implemented by the monitor to selectively determine which access point with which to associate. At block 302, the radio 106 measures the RSSI value of at least one wireless access point 124a and buffers the received RSSI value every 1 second into memory 112. At block 303, the control processor 102 obtains an average RSSI value by filtering the buffered RSSI values with a 4 tap moving averaging filter to eliminate transient values. The control processor 102, at block 304, compares the RSSI average value to a threshold value (e.g. −75 dBm).

If the comparison at block 304 determines that the RSSI average value is below the threshold RSSI value, the control processor 102 determines if a scan timer that scans for additional access points is running at block 305. If the determination at block 305 is negative, the control processor 102 activates the scan timer at block 307. The scanning algorithm automatically determines if the monitor will remain associated with a current access point 124a or roam to a different access point 124b. This algorithm runs concurrently with the algorithm described with respect to FIG. 3 and will be separately detailed below with respect to FIG. 4.

Referring back to block 304, if the comparison determines that the RSSI average value is greater than the threshold value, the control processor 102 determines if the scan timer is running at block 306. If the scan timer is running, after determining the RSSI average value exceeds the threshold RSSI value, the scan timer is deactivated by the control processor 102 at block 308.

If the determination in block 304 is below the threshold RSSI value and the determination in block 305 indicates that the scan timer is active, then the algorithm proceeds in FIG. 5. Additionally, if the determination in block 304 is above the threshold RSSI value and the determination in block 306 indicates that the scan timer is inactive, then the algorithm similarly proceeds in FIG. 5.

Figure 4:
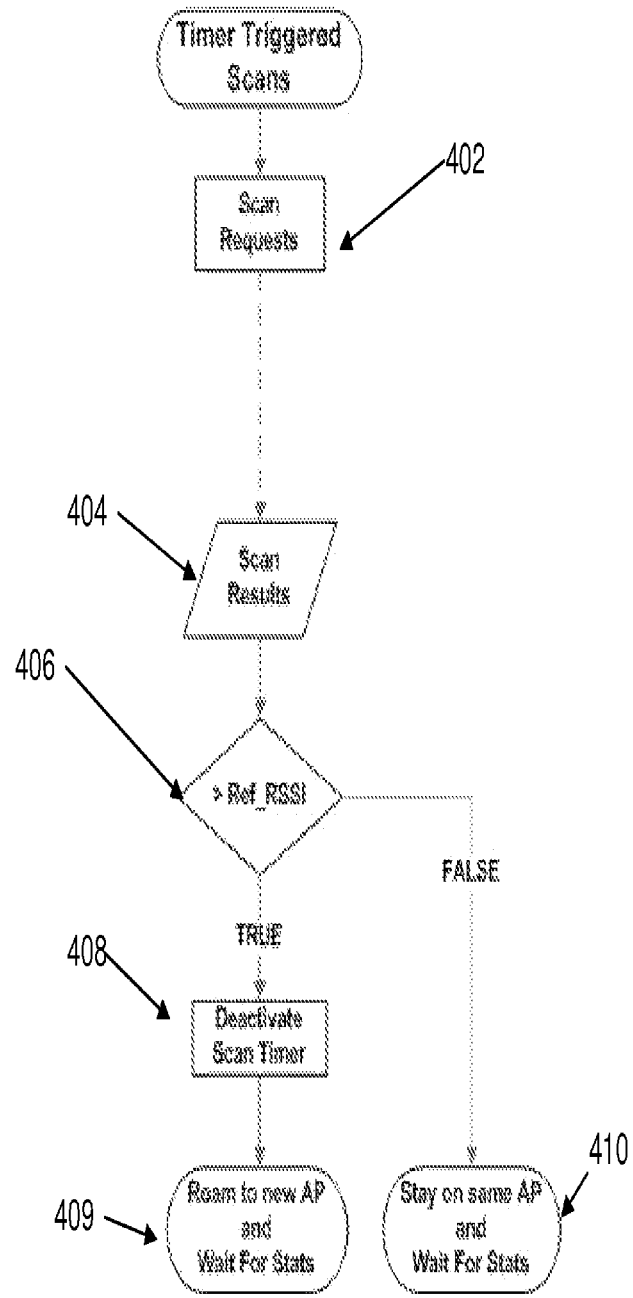
FIG. 4 is a flow diagram detailing an operation of a portable patient monitoring device according to invention principles.

FIG. 4 describes an exemplary time triggered scanning algorithm to determine with which access point a respective monitor 100 should associate. A scan request searching for additional access points is initiated at block 402. The scan request actively searches to obtain RSSI values for a plurality of access points different from the access point with which the monitor 100 is currently associated. A result of the scan producing a set of additional access points is obtained at block 404. The control processor 102 identifies other access points from having a higher RSSI level from within the set of additional access points and compares single RSSI values from each respective access point that have responded to the scan. The control processor 102 selects an access point having the highest RSSI value from the set of additional access points. The RSSI of the selected access point is compared with a reference RSSI value in block 406. The reference RSSI value equals the average RSSI of the access point the monitor is associated with plus 5 or, if the monitor is not associated with an access point, the reference RSSI is the greatest RSSI value of list of access points that have responded to the monitor's scan. The plus 5 provides hysteresis that advantageously prevents repeatedly associating and disassociating between two different access points if two available access points have similar RSSI values that are close to the threshold. If the RSSI value of the selected access point is greater than the reference RSSI value, the scan timer is deactivated in block 408 and the radio 106 is caused to roam to the selected access point. If the RSSI value of the selected access point is less than the reference RSSI value as determined at block 406, the radio 106 remains associated with the current access point. Alternatively, the control processor 102 may select a different access point from the set of access points in the result in block 404 and repeat the RSSI comparison described in block 406 until a determination to roam to a different access point is made.

Figure 5:
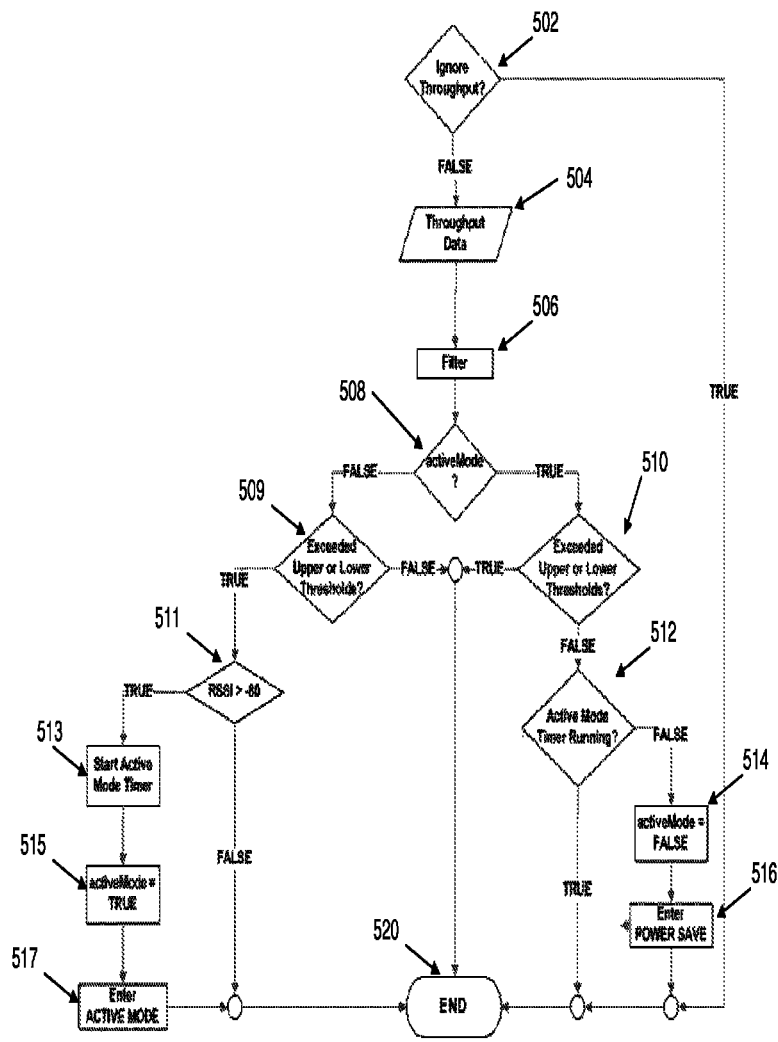
FIG. 5 is a flow diagram detailing an operation of a portable patient monitoring device according to invention principles.

FIG. 5 is an exemplary algorithm for determining whether the radio 106 of the monitor 100 should switch from power save mode to the active transmission mode. At block 502, the control processor 102 automatically analyzes device-specific information to determine whether or not to ignore a measurement of throughput data at a given time. For example, the determination in 502 may include information identifying whether or not the monitor is at least one of (a) being charged in a charging cradle; (b) not actively associated with a particular patient; (c) not connected with a central station; and (d) configured not to monitor throughput data values.

If block 502 determines that throughput data measurements should be ignored, the algorithm ends at block 520. If the determination at block 502 is false indicating the measurement should not be ignored, the baseband IC 204 of the radio obtains a measurement of throughput data at block 504. The throughput data measurement may include bytes transmitted per second and/or bytes received per second. The throughput data measured at block 504 is filtered at block 506 to obtain an average data throughput value. The average data throughput value is obtained by filtering the throughput measurement data using a four tap moving averaging filter to eliminate transient throughput data values. The filtering applied in block 506 is a smoothing filter and is performed over throughput data received by the RF transceiver 202 of the radio 106 having a duration of substantially three seconds (3 s). Once the average throughput data value is obtained, the baseband IC 204 determines if the radio 106 is in the active transmission mode in block 508.

If it is determined, in block 508, that the radio is in active transmission mode, the baseband IC 204 determines whether or not the average throughput data value exceeds an upper threshold of an acceptable throughput data range or is below a lower threshold of an acceptable throughput data range in block 510. If the determination in block 510 is true indicating the data transmission is not acceptable, then the algorithm ends at block 520 by reverting back to block 302 in FIG. 3 or, alternatively block 602 in FIG. 6 described below. If the average throughput data value is within the acceptable range of throughput data values, the control processor 102 determines if an active mode timer is running in block 512. If the active mode timer is running, then the algorithm ends at block 520 by reverting back to block 302 in FIG. 3 or, alternatively block 602 in FIG. 6. If the active mode timer is determined in block 512 to be expired or inactive, the control processor 102 provides a control signal in block 514 including a flag indicating that the radio 106 should exit active mode and revert back to power save mode in block 516. Upon the radio 106 entering power save mode in block 516, the algorithm ends at block 520 by reverting back to block 302 in FIG. 3 or, alternatively block 602 in FIG. 6.

Referring back to block 508, if it is determined that the radio is in power save mode (e.g. not in active transmission mode), the baseband IC 204 determines whether or not the average throughput data value exceeds an upper threshold of an acceptable throughput data range or is below a lower threshold of an acceptable throughput data range in block 509. If the determination in block 509 is false indicating that the throughput data value is within the acceptable range, then the algorithm ends at block 520 by reverting back to block 302 in FIG. 3 or, alternatively moves on to block 602 in FIG. 6 described below. If the determination in block 509 yields an average throughput data value outside of a band defined by the upper threshold and lower threshold of acceptable throughput data values, the control processor 102 compares an RSSI average value with a second RSSI threshold (default=−80 dBm) at block 511. The determination at block 511 functions as a check to make sure the cause of the throughput data being outside the acceptable range is not due to the need to roam to a different access point. If the signal strength is insufficient then the cause of transmission gap as evidenced by the throughput data value being outside the acceptable range may be due to the need to connect to an access point that is more proximate to the monitor's current location. If the determination at block 511 yields a result indicating that the RSSI value is below the second threshold value, then the algorithm ends at block 520 by reverting back to block 302 in FIG. 3 or, alternatively moves on to block 602 in FIG. 6 described below.

If the determination in block 511 indicates that the RSSI value is greater than the second threshold, it is indicative that the monitor does not need to roam to a different access point. Moreover, the active mode timer is initiated in block 515 and an instruction including a flag indicating that the radio should transition from power save mode to active transmission mode is provided to the baseband IC 204 of the radio 106. Upon receipt of the instruction in block 515, the radio 106 is caused to enter the active transmission mode for the predetermined amount of time thereby enabling continual transmission and receipt of data between the monitor 100 and the access point 124*a* to which it is connected and reduces a likelihood of that a transmission gaps will occur.

Figure 6:
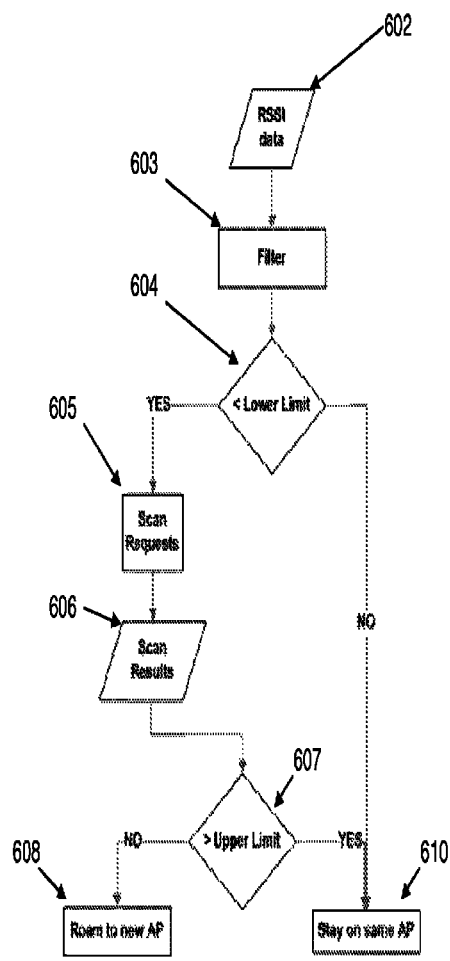
FIG. 6 is a flow diagram detailing an operation of a portable patient monitoring device according to invention principles.

FIG. 6 is an alternate roaming algorithm that may be implemented by the monitor to selectively determine which access point with which to associate. The activities described in FIG. 6 may occur instead of the activities described above in FIG. 3 or in addition to the activities described in FIG. 3. At block 602, the radio 106 receives RSSI data from at least one wireless access point 124*a* and buffers the received RSSI data every 1 second into memory 112. At block 603, the control processor 102 obtains an average RSSI value by filtering the buffered RSSI data with a 4 tap moving averaging filter to eliminate transient values. The control processor 102, at block 604, compares the RSSI average value to a threshold value (e.g. −75 dBm). If the calculated RSSI average value is greater than the threshold value, it is indicative of the monitor 100 being associated with and able to communicate with a proper access point and thus the monitor remains associated with the access point in block 610.

If the RSSI average value compared to the threshold in block 604 is below the lower threshold, then a scan request searching for additional access points is initiated at block 605. The scan request at block 605 actively searches to obtain RSSI values for a plurality of access points different from the access point that the monitor 100 is currently associated. A result of the scan is obtained at block 606 to produce a set of additional access points. The control processor 102 identifies another access point from within the set of additional access points having a higher RSSI power level and compares single RSSI values from each respective access point that have responded to the scan. The control processor 102 selects an access point having the highest RSSI value from the set. The RSSI of the selected access point is compared with an upper threshold RSSI value in block 607. If the RSSI value of the selected access point is greater than the threshold value, then the monitor remains on the currently associated access point in block 610. If the comparison in block 607 produces a result whereby the selected RSSI value is below the threshold, then the monitor initiates a roaming sequence and roams to the selected access point in block 608.

The portable patient monitoring apparatus is able to advantageously reduce the number of transmission gaps between itself and an access point that is connected to a central monitoring station. In conjunction with a roaming algorithm that selectively determines with which access point the monitor should connect, measurement of a data throughput over a transmission and reception channel is taken. In response to measuring the data throughput characteristics measured, the radio is automatically caused to go from a power save mode to an active transmission mode for a predetermined duration of time when the data throughput characteristics satisfy predetermined criteria. This automatic transition into active mode for the predetermined amount of time advantageously enables immediate bidirectional communication between the monitor and a respective access point thereby insuring that data scheduled to be transferred therebetween occurs as intended. This minimizes any gaps in data transmission that may occur when the monitor is in power save mode and fails to awake in time to at least one transmit data to and receive data from a respective access point or an access point fails to transmit a beacon.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. An apparatus for reducing gaps in data transmission between a device and at least one wireless access point, the apparatus comprising:
   a radio that enables bidirectional data communication between the device and the at least one wireless access point, the radio being able to operate in a power save mode and an active transmission mode; and
   a control processor that selectively monitors an amount of data being transmitted between the radio and the at least one wireless access point to predict an occurrence of a gap in data transmission between the device and the at least one access point, the control processor, in response to predicting a gap in data transmission, automatically switches an operational mode of the radio from the power save mode to the active transmission mode for a predetermined amount of time enabling communication between the device and the at least one wireless access point for the predetermined amount of time;
   wherein said control processor predicts an occurrence of a gap in data transmission by comparing a monitored amount of data to a predefined range of data amounts to determine whether the monitored amount of data is at least one of below a lower limit of the predefined range or above an upper limit of the predefined range.

2. The apparatus according to claim 1, wherein
   said radio is an radio frequency (RF) radio able to communicate via at least one of (a) IEEE 802.11a protocol; (b)

IEEE 802.11b protocol; (c) IEEE 802.11d protocol; (d) IEEE 802.11g protocol; (e) IEEE 802.11i protocol; or (f) IEEE 802.11n protocol.

3. The apparatus according to claim 1, wherein said data is throughput data.

4. The apparatus according to claim 1, wherein said control processor selectively monitors a type and amount of data over at least one of a transmission channel or a reception channel.

5. The apparatus according to claim 1, wherein said control processor automatically switches an operational mode of the radio from active transmission mode to power save mode in response to an expiration of the predetermined amount of time.

6. The apparatus according to claim 1, wherein said control processor continually monitors a type and an amount of data being transmitted between the radio and the at least one wireless access point during the predetermined amount of time and automatically switches the operational mode of the radio from active transmission mode to power save mode prior to the expiration of the predetermined amount of time if the monitored type and amount of data meet a predetermined condition.

7. The apparatus according to claim 1, wherein said control processor compares a signal strength indicator received by the radio from the at least one wireless access point to a threshold signal strength value in response to predicting a gap in data transmission and automatically initiates a roaming algorithm enabling the device to search for and connect to a different wireless access point if the indicator has a value less than the threshold value, and switches the operational mode of the radio from the power save mode to the active mode if the indicator has a value greater than the threshold value.

8. The apparatus according to claim 1, wherein said control processor automatically identifies an operating mode of the device to selectively determine if a type and an amount of data being transmitted between the radio and the at least one access point should be monitored and automatically disabling the monitoring of the type and amount of data in response to the identified operating mode.

9. The apparatus according to claim 1, wherein said device is a patient monitoring device coupled to a patient that enables patient ambulation around a healthcare facility and selectively monitors at least one patient parameter.

10. The apparatus according to claim 1, wherein said control processor selectively monitors at least one of a type and amount of the data being transmitted between the radio and the at least one wireless access point.

11. The apparatus according to claim 1, wherein said control processor enables bidirectional communication upon automatically switching the operational mode of the radio from the power save mode to the active transmission mode.

12. A method of reducing gaps in data transmission between a device and at least one wireless access point, the method comprising:
monitoring, by a control processor, an amount of data being transmitted between a radio of the device and the at least one wireless access point;
predicting an occurrence of a gap in data transmission between the device and the at least one access point; and
automatically switching an operational mode of the radio from power save mode to active transmission mode for a predetermined amount of time in response to predicting a gap in data transmission;
thereby enabling communication between the device and the at least one wireless access point for the predetermined amount of time;
wherein said control processor predicts an occurrence of a gap in data transmission by comparing a monitored amount of data to a predefined range of data amounts to determine whether a monitored amount of data is at least one of below a lower limit of the predefined range or above an upper limit of the predefined range.

13. The method according to claim 12, wherein the radio is an radio frequency (RF) radio able to communicate via at least one of (a) IEEE 802.11a protocol; (b) IEEE 802.11b protocol; (c) IEEE 802.11d protocol; (d) IEEE 802.11g protocol; (e) IEEE 802.11i protocol; or (f) IEEE 802.11n protocol.

14. The method according to claim 12, wherein said activity of monitoring includes monitoring throughput data.

15. The method according to claim 12, wherein said activity of monitoring further comprises monitoring a type and amount of data over at least one of a transmission channel and a reception channel.

16. The method according to claim 12, further comprising:
automatically switching an operational mode of the radio from active transmission mode to power save mode in response to an expiration of the predetermined amount of time.

17. The method according to claim 12, further comprising:
continually monitoring a type and the amount of data being transmitted between the radio and the at least one wireless access point during the predetermined amount of time; and
automatically switching the operational mode of the radio from active transmission mode to power save mode prior to the expiration of the predetermined amount of time if the monitored type and amount of data meet a predetermined condition.

18. The method according to claim 12, further comprising:
comparing a signal strength indicator received by the radio from the at least one wireless access point to a threshold signal strength value in response to predicting a gap in data transmission and automatically initiating a roaming algorithm enabling the device to search for and connect to a different wireless access point if the indicator has a value less than the threshold value, and
switching the operational mode of the radio from power save mode to the active mode if the indicator has a value that is greater than the threshold value.

19. The method according to claim 12, further comprising:
automatically identifying an operating mode of the device to selectively determine if a type and the amount of data being transmitted between the radio and the at least one access point should be monitored and automatically disabling the monitoring of the type and amount of data in response to the identified operating mode.

20. The method according to claim 12, wherein said monitoring monitors at least one of a type or an amount of the data being transmitted between the radio and the at least one wireless access point.

21. The method according to claim 12, wherein said automatically switching enables bidirectional communication between the device and the at least one wireless access point.

22. An apparatus for reducing gaps in data transmission between a device and at least one wireless access point, the apparatus comprising:
- a radio that enables bidirectional data communication between the device and the at least one wireless access point, the radio being able to operate in a power save mode and an active transmission mode; and
- a control processor that selectively monitors an amount of data being transmitted between the radio and the at least one wireless access point to detect an occurrence of a gap in data transmission between the device and the at least one access point, the control processor, in response to detecting a gap in data transmission, automatically switches an operational mode of the radio from the power save mode to the active transmission mode for a predetermined amount of time enabling communication between the device and the at least one wireless access point for the predetermined amount of time;
- wherein said control processor predicts an occurrence of a gap in data transmission by comparing a monitored amount of data to a predefined range of data amounts to determine whether a monitored amount of data is at least one of below a lower limit of the predefined range or above an upper limit of the predefined range.

* * * * *